United States Patent [19]
Rakhit et al.

[11] Patent Number: 5,095,004
[45] Date of Patent: Mar. 10, 1992

[54] FLUORINE CONTAINING ATRIAL NATRIURETIC PEPTIDES

[75] Inventors: Sumanas Rakhit, Dollard-des-Ormeaux; Mahesh H. Goghari, Laval, both of Canada

[73] Assignee: Bio-Mega Inc., Quebec, Canada

[21] Appl. No.: 166,526

[22] Filed: Mar. 14, 1988

[30] Foreign Application Priority Data

Mar. 25, 1987 [CA] Canada .................................. 532982
Jul. 15, 1987 [CA] Canada .................................. 542192

[51] Int. Cl.[5] .................. A61K 37/24; A61K 37/02; C07K 7/10
[52] U.S. Cl. ........................... 514/12; 514/13; 530/317; 530/324; 530/325; 530/326
[58] Field of Search .............. 514/13, 12; 530/324, 530/325, 326, 317

[56] References Cited

FOREIGN PATENT DOCUMENTS

| | | | |
|---|---|---|---|
| 0173557 | 3/1986 | European Pat. Off. | 514/12 |
| 0182984 | 6/1986 | European Pat. Off. | 514/12 |
| 0189084 | 7/1986 | European Pat. Off. | 514/12 |
| 61-161299 | 7/1986 | Japan | 514/12 |
| 61-233698 | 10/1986 | Japan | 514/12 |
| 61-243100 | 10/1986 | Japan | 514/12 |
| 8504870 | 11/1985 | PCT Int'l Appl. | 514/12 |
| 8504872 | 11/1985 | PCT Int'l Appl. | 514/12 |

OTHER PUBLICATIONS

A. J. De Bold et al., Life Sciences, 28, 89 (1981).
M. Cantin and J. Genest, Endocrine Reviews, 6, 107 (1985).
J. D. Mogannam et al., Abstracts fo the First World Congress on Biologically Active Atrial Peptides, American Society of Hypertension, May 31–Jun. 1, 1986, New York, N.Y., p. 108A.
P. W. Schiller et al., Biochemical and Biophysical Research Communications, 143, 499 (1987).

*Primary Examiner*—Howard E. Schain
*Assistant Examiner*—Susan M. Perkins
*Attorney, Agent, or Firm*—Foley & Lardner

[57] ABSTRACT

Disclosed herein are derivatives of atrial natriuretic peptides which are characterized by having (at position 124 or at positions 106 and 124) a phenylalanyl residue bearing a fluoro or trifluoromethyl substituent on the aromatic portion thereof. Optionally, the exocyclic N-terminal peptide segment and the first cystienyl residue (at position 105) are replaced by an optionally substituted thioalkanoyl residue. The derivatives possess useful diuretic, natriuretic and antihypertensive activities.

10 Claims, No Drawings

FLUORINE CONTAINING ATRIAL NATRIURETIC PEPTIDES

FIELD OF THE INVENTION

This invention relates to derivatives of atrial natriuretic peptides (ANP's) having diuretic, natriuretic and blood pressure lowering effects. More specifically, this invention relates to fluorine containing derivatives of atrial natriuretic peptides, to processes for their production, to pharmaceutical compositions of the derivatives, and to methods of using the derivatives to treat hypertension and to treat pathological conditions characterized by an imbalance of body fluids and/or electrolytes such as congestive heart failure, edema and cirrhosis of the liver.

BACKGROUND OF THE INVENTION

Ever since A. J. de Bold et al., Life Sciences, 28, 89 (19-81) reported that an injection of a crude extract of rat atrial myocardium produced an immediate and potent diuretic response in the rat, a great deal of attention has been given to the elucidation of the active principle responsible for this effect, and to understanding the role of the active principle in nature's regulation of body fluid volume and blood pressure. For a review of these developments, see M. Cantin and J. Genest, Endocrine Reviews, 6, 107 (1985). As a result, the active principle in the rat atrium has been shown to be derived from a prohormone containing 152 amino acids. In human atrium, a corresponding prohormone containing 151 amino acids has been identified. Subsequent investigations have established that fragments of the prohormones containing from about 20 to 33 amino acids are more potent than the prohormones themselves, provided that the fragments still contain the C-terminus portion and the cyclic structure of the prohormone. The cyclic structure results from an intramolecular disulfide bridge formed between two half cystine residues at positions 105 and 121 of the peptide sequence. An example of such fragment of the rat prohormone is rANP(101-126) which has the following structure:

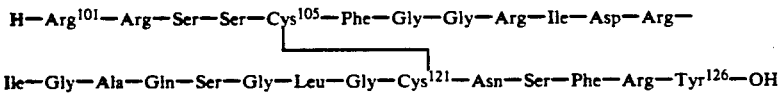

The corresponding fragment of the human prohormone, hANP-(101-126), has the same structure except for the replacement of the isoleucyl residue at 110 by a methionyl residue.

Chemists now have synthesized the smaller, more active atrial peptides (i.e. fragments) thus making them readily available for extensive biological investigations and for possible development as diuretic and antihypertensive agents. However, the development of the natural peptides is hampered by their rapid decomposition in vivo by enzymatic processes. Accordingly several investigators are now looking at derivatives or analogs of the natural atrial peptides as a source for potential drugs with improved stability, potency and duration of action over the natural peptides. For example, see L. Johnson et al., PCT patent application WO85/04870, published Nov. 7, 1985; J. Rivier and F. Edouard, PCT patent application WO85/04872, published Nov. 7, 1985; S. Sakakibara, European patent application 85306085.3, published Mar. 5, 1986; and J. D. Mogannam et al. Abstracts of the First World Congress on Biologically Active Atrial Peptides, American Society of Hypertension, May 31–June 1, 1986, New York, N.Y. p. 108A, Japanese patent application 61161299, published July 21, 1986; Japanese patent application 61233698, published Oct. 17, 1986; and Japanese patent application 61243100. published Oct. 29, 1986.

The present application discloses new atrial peptide derivatives having a favorable biological profile which renders them useful as diuretic and antihypertensive agents.

SUMMARY OF THE INVENTION

The atrial peptide derivatives of this inventions are represented by formula 1

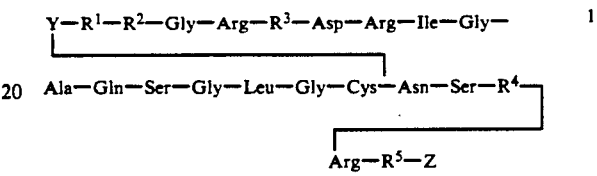

wherein
$R^1$ is Phe, 2FPhe, 3FPhe, 4FPhe, 2CF$_3$Phe, 3CF$_3$Phe or 4CF$_3$Phe;
$R^2$ is Gly, Ala or D-Ala;
$R^3$ is Ile or Met;
$R^4$ is 2FPhe, 3FPhe, 4FPhe, 2CF$_3$Phe, 3CF$_3$Phe or 4CF$_3$Phe;
$R^5$ is Tyr or des-$R^5$;

wherein $R^6$ is H-Ser-Ser, H-Arg-Ser-Ser, H-Arg-Arg-Ser-Ser, H-Leu-Arg-Arg-Ser-Ser or H-Ser-Leu-Arg-Arg-Ser-Ser; and Z is hydroxy, amino or lower alkylamino;
or a therapeutically acceptable salt thereof.

A preferred group of the peptide derivatives of this invention is represented by formula 1 wherein $R^1$, $R^2$, $R^3$ and $R^4$ and $R^5$ are as defined hereinabove,

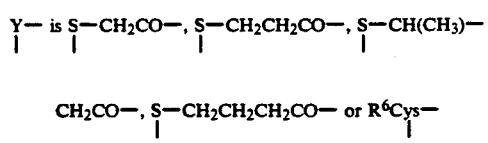

wherein $R^6$ is as defined hereinabove, and Z is hydroxy or amino; or a therapeutically acceptable salt thereof.

A more preferred group of the peptide derivatives is represented by formula 1 wherein $R^1$ is Phe, 2FPhe, 3FPhe, 4FPhe or 4CF$_3$Phe, $R^2$ is Gly or D-Ala, $R^3$ is Ile or Met, $R^4$ is 2FPhe, 3FPhe, 4FPhe or 4CF$_3$Phe, $R^5$ is Tyr or des-$R^5$,

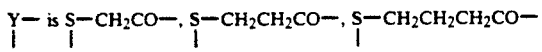

or R⁵-Cys- wherein R⁵ is as defined hereinabove, and Z is hydroxy or amino; or a therapeutically acceptable salt thereof.

A most preferred group of the peptide derivatives is represented by formula 1 wherein R¹ is Phe, 3FPhe, 4FPhe or 4CF₃-Phe, R² is Gly, R³ is Ile or Met, R⁴ is 3FPhe, 4FPhe or 4CF₃Phe, R⁵ is Tyr or des-R⁵,

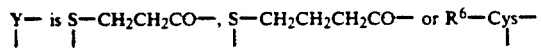

wherein R⁶ is as defined herein above and Z is hydroxy or amino; or a therapeutically acceptable salt thereof.

Included within the scope of this invention is a pharmaceutical composition comprising a peptide derivative of formula 1, or a therapeutically acceptable salt thereof, and a pharmaceutically acceptable carrier.

The administration of the peptide derivatives, or pharmaceutically acceptable addition salts thereof, to mammals in accordance with the invention regulates urine production, relaxes intestinal smooth muscles, relieves hypertension and acts to counteract pathological conditions associated with cirrhosis of the liver and congestive heart failure. Thus, included within the scope of this invention is a method of effecting diuresis and/or natriuresis in a mammal which comprises administering to the mammal a therapeutically effective amount of a peptide derivatives of formula 1, or a therapeutically acceptable salt thereof.

Also included is a method of treating hypertension in a hypertensive mammal which comprises administering to the mammal an antihypertensively effective amount of a peptide derivative of formula 1, or a therapeutically acceptable salt thereof.

Processes for preparing the peptide derivatives of formula 1 are described hereinafter.

Details of the Invention

For convenience, the peptide derivatives of this application hereinafter are designated simply as peptides.

The term 'residue' with reference to an amino acid means a radical derived from the corresponding α-amino acid by eliminating the hydroxyl of the carboxyl group and one hydrogen of the α-amino group.

In general, the abbreviations used herein for designating the amino acids and the protective groups are based on recommendations of the IUPAC-IUB Commission on Biochemical Nomenclature, see Biochemistry, 11, 1726-1732 (1972). For instance, Met, Met(O), Gln, Ala, Gly, Ile, Arg, Asp, Phe, Ser, Leu, Cys, Asn and Tyr represent the 'residues' of L-methionine, L-methionine sulfoxide, L-glutamine, L-alanine, glycine, L-isoleucine, L-arginine, L-aspartic acid, L-phenylalanine, L-serine, L-leucine, L-cysteine, L-asparagine and L-tyrosine, respectively.

The symbol "2FPhe" represents the 'residue' 2-fluoro-L-phenylalanyl, i.e. (S)-α-amino-(2-fluorobenzene)propanoyl. Similarly, 3FPhe, 4FPhe, 2CF₃Phe, 3CF₃Phe and 4CF₃Phe represent the residues 3-fluoro-L-phenylalanyl, 4-fluoro-L-phenylalanyl, 2-(trifluoromethyl)-L-phenylalanyl, 3-(trifluoro-methyl)-L-phenylalanyl and 4-(trifluoromethyl)-L-phenylalanyl, respectively.

The term 'lower alkyl' as used herein means straight chain alkyl radicals containing one to four carbon atoms and branched chain alkyl radicals containing three or four carbon atoms and includes methyl, ethyl, propyl, butyl, 1-methylethyl, 2-methylpropyl and 1,1-dimethylethyl.

The term 'lower alkylene' as used herein means both straight and branched chain divalent alkylene radicals derived from corresponding aliphatic hydrocarbons containing from one to six carbon atoms by removal of two hydrogen atoms, and includes, for example, CH₂, CH₂CH₂, CH(CH₃)CH₂, CH₂CH(CH₃), CH(C₂H₅)CH₂, CH₂CH₂CH₂ and CH₂CH(n—C₃H₇)CH₂. The enantiomers of those lower alkylenes containing one or two asymmetric carbon atoms are included within the meaning of lower alkylene.

The term 'pharmaceutically acceptable carrier' as used herein means a non-toxic, generally inert vehicle for the active ingredient which does not adversely affect the ingredient.

The peptides of formula 1 are prepared by forming a linear protected intermediate of formula 2

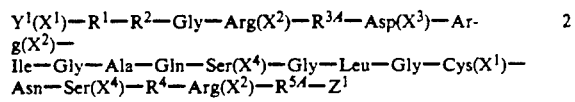

wherein R¹, R² and R⁴ are as defined herein, X¹ is a protective group for a sulfhydryl, preferably benzyl, 4-methylbenzyl, acetamidomethyl or 2,6-dichlorobenzyl, X² is a protective group for the guanidino group of Arg, preferably tosyl or nitro; X³ is a protective group for the β-carboxyl of Asp, preferably benzyl, cyclohexyl or 2,6-dichlorobenzyl, X⁴ is a protective group for the hydroxy group of Ser, preferably benzyl, Y¹ is S-(lower alkylene)-CO or R⁷-cys wherein R⁷ is H-Ser(X⁴)-Ser(X⁴), H-Arg(X²)-Ser(X⁴)-Ser(X⁴), H-Arg(X²)-Arg(X²)-Ser(X⁴)-Ser(X⁴), H-Leu-Arg(X²)-Arg(X²)-Ser(X⁴)-Ser(X⁴) or H-Ser(H⁴)-Leu-Arg(X²)-Arg-X²)-Ser-(X⁴)-Ser(X⁴) wherein X² and X⁴ are protective groups as defined hereinabove, R³⁴ is Ile, Met or Met(0), R⁵⁴ is des-R⁵⁴ or Tyr(X⁵) wherein X⁵ is a protective group for the hydroxyl of Tyr, preferably benzyl or 2-bromobenzyloxy-carbonyl, and Z¹ is hydroxy, amino, lower alkylamino or a linking group, used in solid phase synthesis, which is linked to a solid resin support, preferably:

OCH₂-(resin support) or NH-(resin support).

The linear protected intermediate of formula 2 can be prepared by a suitable method such as by exclusively solid phase techniques, by partial solid phase techniques and/or by fragment condensation, or by classical solution couplings. For example, the techniques of exclusively solid phase synthesis are described by J. M. Stewart and J. D. Young in the textbook 'Solid Phase Peptide Synthesis', W. H. Freeman & Co., San Francisco, 1969, pp. 40-49. The fragment condensation method is exemplified by the disclosure of Canadian patent 1,178,950, issued Dec. 4, 1984. Other available syntheses are exemplified by U.S. Pat. No. 3,842,067, issued Oct. 15, 1974, and U.S. Pat. No. 3,862,925, issued Jan. 28, 1975.

The disclosures of the aforementioned publication by Stewart and Young, Canadian patent 1,178,950 and U.S. Pat. Nos. 3,842,067 and 3,862,925 are herein incorporated by reference.

The ω-mercaptoalkanoyl residue, S-(lower alkylene)-CO, of the intermediate of formula 2, although not an amino acid residue, is incorporated into the intermediate in the same manner as one of the amino acid residues. Thus, by using a protected ω-mercaptoalkanoic acid at the appropriate stage of the process the linear intermediate of formula 2 where $Y^1$ is S-(lower alkylene)-CO is realized.

The protected or unprotected ω-mercaptoalkanoic acids are commercially available, well know or can be prepared by known methods. For example, 3-methyl-3-(benzylthio)butanoic acid has been described by H. Schulz and V. du Vigneaud, J. Med. Chem., 9, 647 (1966).

The various fluorine containing amino acids, for example, 4-fluoro-L-phenylalanine, are commercially available (Asahi Glass Co. Ltd., Tokyo, Japan).

Returning to the general processes for the intermediate of formula 2, a common feature of the processes is the protection of the labile side chain groups of the various amino acid residues, and if present the sulfhydryl group of the ω-mercaptoalkanoyl residue, with suitable protective groups which will prevent a chemical reaction from occurring at that site until the protective group is ultimately removed. Usually also common is the protection of an α-amino group on an amino acid or a fragment while that entity reacts at the carboxyl group, followed by the selective removal of the α-amino protecting group to allow subsequent reaction to take place at that location.

When preparing the peptides of formula 1 wherein $R^3$ is Met, a methionine sulfoxide reactant can be used optionally to incorporate the methionyl residue into the assembled peptide. After the amino acids residues, and the ω-mercaptoalkanoyl residue, if required, have been assembled into the desired sequence, in this instance, the methionine sulfoxide residue is reduced to its corresponding methionyl residue. A convenient method for accomplishing this reduction is to subject the intermediate of formula 2 wherein $R^3$ is Met(O) to the hydrogen-fluoride-dimethyl sulfide reagent of J. P. Tam et al., J. Amer. Chem. Soc., 105, 6442 (1983) to obtain the corresponding intermediate of formula 2 wherein $R^{3A}$ is Met. In a broader sense, therefore, the oxygen of the sulfoxide represents an optional side chain protecting group.

In an embodiment of the exclusively solid phase method, a linear protected intermediate of formula 2 is prepared as follows: α-amino protected tyrosine provided with protection of its hydroxy group, preferably $N^\alpha$-(t-butyloxycarbonyl)-O-(2-bromobenzyloxycarbonyl)tyrosine, is coupled to an α-(phenyl-acetamido)-benzyl-benzhydrylamine resin in the presence of potassium fluoride or cesium chloride to give the corresponding solid support resin having the first amino acid (in protected form) linked thereto. Alternatively, an oxymethylated solid resin support with the incorporated protected amino acid may be obtained commercially and used as the starting material. In either event, the next step is the removal of the α-amino protective group of the incorporated amino acid to give the free α-amino group. In the instance where the α-amino protective group is a t-butyloxycarbonyl, trifluoroacetic acid in methylene chloride or chloroform, or hydrochloric acid in dioxane, is used to effect the deprotection. The deprotection is carried out at a temperature between about 0° C. and room temperature. Other standard cleaving reagents and conditions for removal of specific α-amino protecting groups may be used as described by E. Schröder and K. Lübke, in "The Peptides", Vol. 1, Academic Press, New York, 1965, pp. 72–75. After removal of the α-amino protecting group from the last mentioned intermediate, the remaining α-amino protected amino acids and if required, the protected ω-mercaptoalkanoic acid, are coupled stepwise in the desired order to obtain the linear protected intermediate of formula 2. Each protected amino acid or the protected ω-mercaptoalkanoic acid is introduced into the reaction system in a one to four fold excess and the coupling is carried out in a medium of methylene chloride, dimethylformamide, or mixtures of dimethylformamide and methylene chloride. In cases where incomplete coupling has occurred, the coupling procedure is repeated before removal of the α-amino protective group, prior to the coupling of the next protected amino acid or the protected ω-mercaptoalkanoic acid. The success of the coupling reaction at each stage of the synthesis is monitored by the ninhydrin reaction as described by E. Kaiser et al., Anal. Biochem., 34, 595 (1970).

The intermediate of formula 2, obtained as described above, is subsequently transformed to give the desired peptides of formula 1 by deprotecting and oxidizing steps which hitherto have been well established for peptide synthesis. More explicitly, the intermediate of formula 2 may be deprotected under conditions which cleave all the side chain protective groups and, if present, the solid resin support with its expendable portion of the linking group, to obtain the corresponding linear form of the final product, i.e. the deprotected linear compound of formula 3

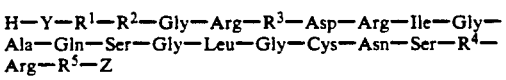

$$H-Y-R^1-R^2-Gly-Arg-R^3-Asp-Arg-Ile-Gly-Ala-Gln-Ser-Gly-Leu-Gly-Cys-Asn-Ser-R^4-Arg-R^5-Z \qquad 3$$

in which $R^1$, $R^2$, $R^3$, $R^4$, $R^5$, Y and Z are as defined hereinbefore.

For example, the intermediate of formula 2 obtained in the preceding embodiment is removed from the resin support by treatment with hydrogen fluoride to give the corresponding deprotected linear compound of formula 3 in which Z is hydroxy. The intermediate of formula 2 can also be separated from the resin by transesterification with a lower alkanol, preferably methanol or ethanol, in the presence of triethylamine. Thereafter, the recovered ester is purified by chromatography. The collected fraction may be subjected to treatment with ammonia or a (lower alkyl)amine to convert the lower alkyl ester to the carboxy-terminal amide (compound 3, Z=amino) or (lower alkyl)amine (compound 3,Z=lower alkylamino). The remaining protective groups are then cleaved by procedures described above, for example by treatment with sodium in liquid ammonia or by hydrogen fluoride. Removal of the protected linear intermediate of formula 2 from the resin support may also be carried out with ammonia to give the corresponding amide, i.e. the linear deprotected compound of formula 3 in which Z is amino.

Alternatively, the linear deprotected compound of formula 3 (Z=amino) can be prepared by a solid phase method using 1% cross-linked benzhydrylamine (BHA) or 4-methylbenzhydrylamine (MBHA) resin, followed by the cleavage of the linear protected intermediate-resin and any required deprotection according to known procedures: for example, see G. R. Matsueda and J. M. Stewart, Peptides, 2, 45 (1981).

Thereafter, the linear deprotected compound of formula 3 in which Z is hydroxy, amino or lower alkylamino is oxidized to give the corresponding desired peptide of formula 1. Any of the known oxidizing agents capable of converting sulfhydryl groups into disulfides can be used; for example, oxygen, thiocyanogen, 1,2-diiodoethane, or preferably, potassium ferricyanide or iodine. In this manner, the two sulfhydryls of the compound of formula 3 undergo an intramolecular coupling to form the disulfide bridge, characteristic of the peptides of formula 1.

In still another alternate embodiment of the deprotecting and oxidizing steps, acetamidomethyl (Acm) is used as the protective group ($X^1$) for the sulfhydryl group. This group being acid and base stable survives the usual deprotection conditions whereupon one is able to obtain a derivative of the linear compound of formula 3 wherein all the protective group are removed except for the acetamidomethyl protective groups on the sulfhydryls to give the corresponding linear compound of formula 3a,

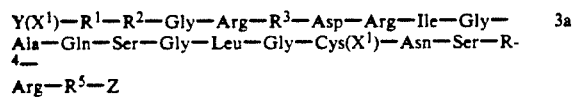

wherein $R^1$, $R^2$, $R^3$, $R^4$, $R^5$, Y and Z are as defined hereinbefore and $X^1$ is Acm.

Subsequent oxidation of this latter derivative with iodine followed by a zinc workup, see for example P. W. Schiller et al., Biochem. Biophys. Res. Commun., 138, 880 (1986), deprotects the sulfhydryls and effects the desired intramolecular disulfide formation to yield the desired peptide of formula 1.

The peptide of formula 1 of this invention can be obtained in the form of therapeutically acceptable salts.

In the instance where a particular peptide has a residue which functions as a base, examples of such salts are those with organic acids, e.g. acetic, lactic, succinic, benzoic, salicyclic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxyl group, example of such salts are those with the sodium, potassium or calcium cations, or with strong organic bases, for example, trietyylamine or N-ethylmopholine.

In general, the therapeutically acceptable salts of the peptides of formula 1 are biologically fully equivalent to the peptides themselves.

The diuretic, natriuretic and antihypertensive properties of the present atrial peptides, or their therapeutically acceptable salts, can be demonstrated in standard pharmacological tests such as those described by Cantin and Genest, supra.

For example, the diuretic and natriuretic activity of the present peptides was demonstrated in vivo in the experimental model employing the conscious normotensive rat in a diuretic assay. More explicitly, normotensive male rats (300–325 g) were anesthetized with halothane. The femoral artery was cannulated for measurements of blood pressure and heart rate and the femoral vein for the administration of the test compounds. The bladder was also cannulated to measure urine flow. After surgery was completed, the animals were placed in restraining cages and allowed to recover from anesthesia for a period of one hour. A Ringer's solution infusion was started at a rate of 1.2 ml per hour. Three control urine samples were collected at 10 minute intervals. The test compound was then infused at a rate varying from 0.5 to 3 μg/kg/min over 30 minutes. Three test samples of urine were collected at 10 minute intervals during the compound infusion. After the test compound had been infused for 30 minutes, Ringer's solution was again infused over 30 minutes and 3 more urine samples were collected. The volume of each urine sample was determined and the electrolyte concentration was measured using a biomedical electrolyte analyser. The animals served as their own controls. The systolic and diastolic blood pressures and the heart rate were determined during each urine collection period.

Table I illustrates the results obtained in the preceding test with the peptide of formula 1 in which $R^1$ is Phe, $R^2$ is Gly, $R^3$ is Met, $R^4$ is 4FPhe, $R^5$ is Tyr,

wherein $R^6$ is H-Ser-Leu-Arg-Arg-Ser-Ser and Z is hydroxy. For convenience in Table 1, and Table II hereinafter, this peptide is designated as (4FPhe[124])hANP(99-126). For comparative purposes, the known human ANP, hANP(99-126), designated as α-hANP by K. Kangawa and H. Matsuo, Biochem. Biophys. Res. Commun., 118, 131 (1984), is included in the tables.

TABLE I

| | | | DIURETIC ASSAY | | | | | | |
|---|---|---|---|---|---|---|---|---|---|
| | | | | | ELECTROLYTE EXCRETION[c] | | | | |
| | DOSE | | URINE VOLUME[b] | | $Na^+$ | | $K^+$ | | $Cl^-$ | |
| COMPOUND[a] | μg/kg/min | n | Control | Treated | Control | Treated | Control | Treated | Control | Treated |
| [4FPhe124] (99-126) | 0.5 | 6 | 0.59 | 0.89 | 17.7 | 73.9 | 38.3 | 54.6 | 38.6 | 116.0 |
| hANP(99-126) | 0.5 | 6 | 0.3 | 0.92 | 17.4 | 60.7 | 43.4 | 60.7 | 46.9 | 110.8 |
| | 0.1 | 6 | 0.71 | 0.65 | 16.0 | 29.6 | 40.3 | 50.3 | 37.6 | 68.3 |

[a]Doses based on the peptide content of the test compound
[b]Given in ml/10 minute collection period - Average of 3 consecutive collections
[c]Given in μmole/10 minute collection period - Average of 3 consecutive collections The blood pressure lowering activity of the peptides was demonstrated by monitoring the blood pressure in hypertensive models such as in renal or DOCA-saline treated hypertensive rats. For example, in applying the DOCA-saline treated rat model, hypertension was induced in rats by administering thereto for a month a weekly subcutaneous injection of 25 mg/kg of desoxycorticosterone acetate, DOCA (Sigma Chemical Co., St-Louis, Mo., U.S.A.) and substituting 1% saline for drinking water. Thereafter, the animals were anesthetized with halothane. After infiltrating the skin with 2% lidocaine solution, the left femoral artery and vein were dissected and cannulated with prefilled polyethylene tubing. Both cannulas were exteriorized at a point near the tail and the main wound sutured. The animals were allowed to recover for at least 30 minutes. Arterial blood pressure was monitored. The test compound was infused for 20 minute intervals at increasing amounts (0.2, 0.5, 1, 2 etc. μg/kg/min) after a control period with saline. A 20 minute infusion of hydralazine (100 μg/kg/min) was used as the standard. Once a well-defined blood pressure lowering effect was achieved, the animals were allowed to recover. The peptides of formula 1, tested according to this procedure at 0.2 to 4 μg/kg/min, produced significant blood pressure lowering effects. For example, 4FPhe$^{124}$hANP(99-126) showed a relative potency of 2.7 on a molar basis as compared to hANP(99-126) in this test.

The vasorelaxant activity of the peptides of formula 1 can be demonstrated in vitro by means of the rat aorta assay. For example, the descending thoracic aorta was excised from New Zealand albino rabbits and placed in Krebs solution at room temperature. The composition of this solution was (g/l): NaCl, 6.9: KCl, 0.35: CaCl$_2$.2-H$_2$O, 0.7: MgSO$_4$.7H$_2$O, 0.29; NaHCO$_3$ 2.1; KHPO$_4$, 0.16; D-glucose, 2.0. The solution was bubbled with 5% carbon dioxide in oxygen (V/V) to maintain its pH at 7.4. The excised aorta was cleaned of extraneous tissue and cut transversely to obtain six 4 mm wide rings. The rings were mounted vertically according to the method described by C. S. Hooker et al., Blood Vessels, 14, 1 (1977). Essentially, a ring was slipped on two stainless steel (0.4 mm diam. wire) 'L'- shaped supports. The lower one was attached to a fixed tissue holder. The higher support was tied by a thread to a force transducer (Model FT.03 Grass Instruments, Quincy, Mass, U.S.A.) connected to a polygraph for isometric recording of tension. By raising the transducer, the ring was placed under tension and then was readjusted, as the tissue relaxed, until a stable 10 g resting tension was attained. During this equilibration period lasting 30 to 45 minutes, the rings were superfused with Krebs solution warmed so that the temperature of the superfusate was 37° to 38° C. when it reached the tissue. The rate of superfusion was set at 15 ml/minute using a multichanneled peristaltic pump. For the rest of the assay, phenylephrine HCl (Sigma Chemical) was added to the superfusate at a concentration of $1 \times 10^{-7}$M. In control experiments this concentration of phenylephrine caused an increase in tension in the rings corresponding to 40 to 60% of their maximal response. This induced increase in tension was maintained throughout the duration of the assay.

The assay was carried out by adding to the trickling superfusate, 3 to 4 cm above an aortic ring, 50 μl of solution of the desired concentration of the test compound. Several doses were administered in increasing order of concentration; at least 3 of the selected doses caused 15 to 85% relaxation of the tissue. The percent relaxation caused by these doses in the six rings from each rabbit was averaged and the regression line calculated. Five rabbits were used for the assay. The dose of the test compound causing a relaxation equal to 50% (EC50) of the phenylephrine-induced tension was determined from each of the 5 linear dose-response regressions. The EC50's were averaged and this value, along with its standard error (S.E.M.), was considered an estimate of the potency of test compound.

The results obtained with 4FPhe$^{124}$hANP(99-126) and hANP(99-126) are shown in Table II.

TABLE II

| | RABBIT AORTA ASSAY | |
|---|---|---|
| PEPTIDE | RELATIVE[a] POTENCY | RELATIVE[b] DURATION |
| [4FPhe$^{124}$]hANP(99-126) | 0.94 | 0.97 |
| hANP(99-126) | 1.0 | 1.0 |

[a]obtained by comparing median effective concentrations (EC50's)
[b]time from onset to 50% recovery at EC50

When the peptides of this invention, or their therapeutically acceptable salts, are employed as diuretic and/or natriuretic agents, or as antihypertensive agents, they usually are administered systemically to warm-blooded animals, e.g. humans, horses or dogs, in combination with pharmaceutical acceptable carriers, the proportion of which is determined by the solubility and chemical nature of the peptide, chosen route of administration and standard biological practice.

For systemic administration, the peptides of formula 1 are administered by either intravenous, subcutaneous or intramuscular injection, in compositions with pharmaceutically acceptable vehicles or carriers. For administration by injection, it is preferred to use the peptides in solution in a sterile aqueous vehicle which may also contain other solutes such as buffers or preservatives as well as sufficient quantities of pharmaceutically acceptable salts or of glucose to make the solution isotonic.

Examples of suitable excipients or carriers are found in standard pharmaceutical texts, e.g. in "Remington's Pharmaceutical Sciences", 16th ed, Mack Publishing Company, Easton, Pa., 1980.

The dosage of the peptides will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the peptides of this invention are most desirably administered at a concentration level that will generally afford diuretic and/or natriuretic effective results, or antihypertensive results, without causing any harmful or deleterious side effects.

When used systemically to effect diuresis and/or natriuresis or to relieve hypertension, the peptide of formula 1 is administered at a dose of 0.05 mcg to 20 mcg per kilogram of body weight per day, although the aforementioned variations will occur. However, a dosage level that is in the range of from about 0.1 mcg to 10 mcg per kilogram of body weight per day is most desirably employed in order to achieve effective results.

It is sometimes desirable to administer the peptides of this invention continuously over prolonged periods of time in long-acting, slow-release, or depot dosage forms. Such dosage forms may either contain a pharmaceutically acceptable salt of the respective peptide having a low degree of solubility in body fluids, for example one of those salts described above, or they may contain the peptide in the form of a water-soluble salt together with a protective carrier which prevents rapid release and decomposition of the peptide. Examples of such formulations are found in standard pharmaceutical texts, e.g., in "Remington's Pharmaceutical Sciences", cited above. Long-acting, slow-release preparations of the peptides of this invention may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York, 1967, pp. 436–456. Such formulations, as well as suspensions of salts of the peptide which are only sparingly soluble in body fluids, are designed to release from about 0.1 mcg to 20 mcg of the peptide per kilogram body weight per day, and are preferably administered by intramuscular injection.

The following examples illustrate further this invention. Abbreviations used in the examples include BOC: t-butyloxycarbonyl; TFA: trifluoroacetic acid: DCC: N,N'-dicyclohexylcarbodiimide; HOBT: 1-hydroxybenzotriazole monohydrate; HF: hydrofluoric acid; and HPLC: high performance liquid chromatography. Solution percentages are calculated on a volume/volume basis unless stated otherwise. The following terms are trademarks: Pharmacia, Vydac, Whatman, Waters and Michel-Miller.

EXAMPLE 1

Preparation of (4FPhe[124])hANP(99-126) having the formula:

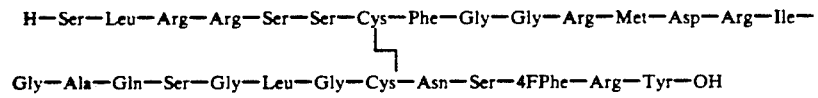

The title compound was synthesized by the solid-phase technique of B. Merrifield, J. Amer. Chem. Soc., 85,2149(1963). The synthesis of the fully protected linear peptide having the correct sequence of amino acids was conducted on an α-(phenylacet-amido)benzyl-benzhydrylamine resin (PAB resin), substitution: 0.406 mM/g, to which N$^\alpha$-(t-butyloxycarbonyl)-O-(2-bromobenzyloxycarboyyl)tyrosine had been linked in the presence of potassium fluoride according to the procedure of E. Giralt et al., Tetrahedron, 37,2007(1981), i.e. BOC-Tyr(2-Br-Z)-PAB- benzhydrylamine resin. The following protocol was used: (a) BOC-deprotection: 25% TFA in chloroform (2 times, firstly for 2 minutes then for 25 minutes); (b) wash: chloroform (3 times for 2 minutes each); (c) neutralization: 10% triethylamine in chloroform (2 times, firstly for 2 minutes then for 10 minutes); (d) amino acid coupling: DCC-HOBT and active ester mediated methods using a three fold molar excess of the preformed symmetrial anhydrides and a reaction time of 3 to 5 hours, and (e) wash: methylene dichloride (3 times for 2 minutes each). With reference to the amino acid coupling, each Asp and Ile residue was double coupled by the symmetrical anhydride method. The Arg residue was double coupled in methylene dichloride/dimethylformamide after activation of the corresponding amino acid with DCC-HOBT. The Gln and Asp residues were double coupled in dimethylformamide via their corresponding 4-nitrophenyl esters. N-(t-butyloxycarbonyl)-4-fluoro-L-phenylalanine, activated with DCC-HOBT, was used to introduce the 4-FPhe residue.

The BOC group gave N$^\alpha$ protection for all aminoacids. Side chain protection was as follows: 2-bromobenzyloxycarbonyl for tyrosine, tosyl for arginine, acetamidomethyl (Acm) for cysteine, cyclohexyl for aspartic acid, the corresponding sulfoxide for methionine, and benzyl for serine. After each coupling, a resin sample was removed during synthesis for a ninydrin test. On completion of the synthesis, the protected peptide-resin was removed from the reaction vessel and dried in vacuo over phosphorus pentoxide and then sodium hydroxide.

The protected peptide first was treated with HF, dimethyl sulfoxide, p-cresol and p-thiocresol (5:20:1:1,v/v/v/v) for 1 hour at 0° C. to remove the oxygen from the methionine sulfoxide residue. The mixture was concentrated under vacuum at 0° C. The residue was treated with HF, p-cresol and p-thiocresol (39:3:1,v/v/v) for 1 hour at 0° C. After rapid removal of the HF reagent under vacuum, the resulting residue was triturated with TFA. The suspended resin was removed by filtration. The filtrate was concentrated in a rotary evaporation. The residue was triturated with diethyl ether and the solid collected by filtration. The solid was dissolved in 5% aqueous acetic acid. The solution was clarified by centrifugation and then lyophlized to give the linear intermediate of formula 3a in which all the protecting groups except the two Acm had been removed.

Purification of the latter compound was effected by reversed-phase chromatography on a Pharmacia octadecasilyl-silica (ODS) column (2.5×40 cm, C-18, Vydac, 30 μ particle size) using a gradiant of 0.06% TFA in H$_2$O and 0.06% TFA in MeOH. The fractions comprising the major peptide peak (UV detection at 254 nm) were pooled and freeze dried. Subsequently, the product was chromatographed on an ion exchange column (CM-23, Whatman) using a linear gradient from 500 ml of 0.01 M ammonium acetate to 500 ml of 0.5 M ammonium acetate. The purity of materials in the fractions was monitored by using analytical reverse phase HPLC (Waters). Desirable fractions were combined and desalted on an ODS column (Michel-Miller, 20 mm×300 mm, C-18, Vydac, 20 μ) to give purified linear compound wherein only the Cys residues remain protected (with Acm).

The linear compound of formula 3a was cyclized to the final product under the following conditions. A 5 mM solution of the compound in 90% aqueous acetic acid was added dropwise within 30 minutes to a 50 mM solution of iodine (50 equivalents with respect to the linear compound) in 90% aqueous acetic acid. The reaction mixture was stirred briskly for 5 hours. Excess iodine was quenched with 1 N aqueous sodium thiosulfate. The mixture was diluted with 3 volumes of water and then freeze dried.

The crude oxidized (cyclized) peptide was desalted and purified by reversed phase, low pressure, HPLC on an ODS column (Michel-Miller, 20 mm×300 mm, C-18, Vydac, 20μ,) using a linear gradient formed by mixing equal volumes (500 ml) of 0.06% TFA in H$_2$O and 0.06% TFA in MeOH. The purity of collected fractions were monitored using analytical reverse phase HPLC (Waters). Pure fractions were combined to give the title compound. Reversed phase HPLC in two different buffer systems and amino acid analysis confirmed that the desired peptide has been obtained in a pure form.

EXAMPLE 2

By following the procedure of example 1, but using N-(t-butyloxycarbonyl)-3-fluoro-L-phenylalanine instead of N-(t-butyloxycarbonyl)-4-fluoro-L-phenylalanine, 3FPhe124hANP(99-126) having the formula

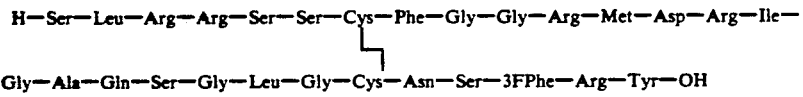

EXAMPLE 3

By following the procedure of example 1, but using N-(t-butyloxycarbonyl)-4-(trifluoromethyl)-L-phenylalanine, instead of N-(t-butyloxycarbonyl)-4-fluoro-L-phenylalanine,(4CF$_3$-Phe$^{124}$)hANP(99-126) having the formula

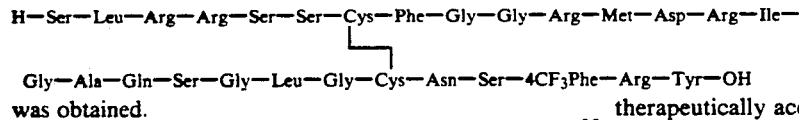

was obtained.

EXAMPLE 4

By following the procedure of example 1, and using the appropriate protected amino acids and finally 3-(acetamidomethylthio)propanoic acid, (SCH$_2$CH$_2$CO$^{105}$, 4FPhe$^{124}$)hANP-(105-126) having the formula

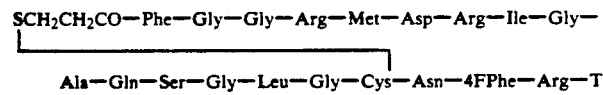

was obtained.

Other examples of the peptides within the scope of this invention include (4FPhe$^{106,124}$)hANP(103-126), 4FPhe$^{124}$, D-Ala$^{107}$)rANP(103-126) (3CF$_3$Phe$^{124}$)hANP(99-126),(SCH$_2$CH$_2$CH$_2$CO$^{105}$,Ala$^{107}$,4FPhe$^{124}$)hANP(105-126), (SCH$_2$CH$_2$CO$^{105}$, 2FPhe$^{106}$)rANP(105-126), (SCH$_2$CH$_2$CO$^{105}$, 3FPhe$^{124}$)rANP(105-126), (SCH$_2$CH$_2$CO$^{105}$, 4FPhe$^{106,124}$)hANP(105-126), (SCH$_2$CH$_2$CO$^{105}$, 4FPhe$^{106}$, D-Ala$^{107}$, 3CF$_3$Phe$^{124}$) rANF(105-126), (D-Ala$^{107}$, 4FPhe$^{124}$)hANP(103-126) and (2FPhe$^{124}$)rANP(103-125).

The embodiments of this invention in which an exclusive property or privilege is claimed are defined as follows:

1. A peptide of formula 1

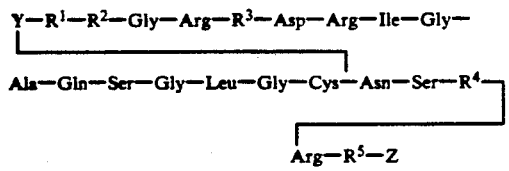

wherein $R^1$ is Phe, 2FPhe, 3FPhe, 4FPhe, 2CF$_3$Phe, 3CF$_3$Phe or 4CF$_3$Phe;
$R^2$ is Gly, Ala or D-Ala;
$R^3$ is Ile or Met;
$R^4$ is 2FPhe, 3FPhe, 4FPhe, 2CF$_3$Phe, 3CF$_3$Phe or 4CF$_3$Phe,
$R^5$ is Tyr or des-$R^5$;
Y- is S-(lower alkylene)-CO-or $R^6$-Cys- wherein $R^6$ is H-Ser-Ser, H-Arg-Ser-Ser, H-Arg-Arg-Ser-Ser, H-Leu-Arg-Arg-Ser-Ser or H-Ser-Leu-Arg-Arg-Ser-Ser; and Z is hydroxy, amino or lower alkylamino; or a therapeutically acceptable salt thereof.

2. A peptide of formula 1 of claim 1 wherein $R^1$, $R^2$, $R^3$, $R^4$ and $R^5$ are as defined in claim 1, Y— is S—CH$_2$CO—,S—CH$_2$CH$_2$CO—, S—CH(CH$_3$)CH$_2$CO—,·S—CH$_2$CH$_2$CH$_2$CO—, or $R^6$—Cys— wherein $R^6$ is as defined in claim 1, and Z is hydroxy or amino; or a therapeutically acceptable salt thereof.

3. A peptide of formula 1 of claim 1 wherein $R^1$ is Phe, 2FPhe, 3FPhe, 4FPhe or 4CF$_3$Phe, $R^2$ is Gly or D-Ala, $R^3$ is Ile or Met, $R^4$ is 2FPhe, 3FPhe, 4FPhe or 4CF$_3$Phe, $R^5$ is Tyr or des-$R^5$, Y— is S—CH$_2$CO—, S—CH$_2$CH$_2$CO—S—CH$_2$CH$_2$CH$_2$CO or $R^6$—Cys— wherein $R^6$ is as defined in claim 1, and Z is hydroxy or amino; or a therapeutically acceptable salt thereof.

4. A peptide of formula 1 of claim 1 wherein $R^1$ is Phe, 3FPhe, 4FPhe or 4CF$_3$Phe, $R^2$ is Gly, $R^3$ is Ile, or Met, $R^4$ is 3FPhe, 4FPhe or 4CF$_3$Phe, $R^5$ is Tyr or des $R^5$, Y— is S—CH$_2$CH$_2$CO—, S—CH$_2$CH$_2$CH$_2$CO—or $R^6$—Cys— wherein $R^6$ is as claimed in claim 1, and Z is hydroxy or amino; or a therapeutically acceptable salt thereof.

5. A peptide selected from the group consisting of a peptide of formula 1 wherein $R^1$ is Phe, $R^2$ is Gly, $R^3$ is Met, $R^4$ is Tyr, Y is H-Ser-Leu-Arg-Arg-Ser-Ser-Cys and Z is hydroxy, a peptide of formula 1 wherein $R^1$ is Phe, $R^2$ is Gly, $R^3$ is Met, $R^5$ is Tyr, Y is H-Ser-Leu-Arg-Arg-Ser-Ser-Cys and Z is hydroxy; a peptide of formula 1 wherein R1 is Phe, $R^2$ is Gly, $R^3$ is Met, $R^4$ is 4CF$_3$Phe, $R^5$ is Tyr and Y is H-Ser-Leu-Arg-Arg-Ser-Ser-Cys; and a peptide of formula 1 wherein $R^1$ is Phe, $R^2$ is Gly, $R^3$ is Met, $R^4$ is 4FPhe, $R^5$ is Tyr, Y is S-CH$_2$CH$_2$CO and Z is hydroxy.

6. A pharmaceutical composition which comprises a peptide of claim 1, or a therapeutically acceptable salt thereof, and a pharmaceutically acceptable carrier.

7. A method for effecting diuresis or natriuresis in a mammal which comprises administering to the mammal a therapeutically effective amount of the peptide of claim 1.

8. A method of treating hypertension in a mammal which comprises administering to the mammal an antihypertensively effective amount of the peptide of claim 1.

9. A process for preparing a peptide of formula 1 of claim 1 which comprises forming a protected peptide of formula 2:

$$Y^1(X^1)-R^1-R^2-Gly-Arg(X^2)-R^{3,4}-Asp(X^3)-Arg(X^2)-$$
$$Ile-Gly-Ala-Gln-Ser(X^4)-Gly-Leu-Gly-Cys(X^1)-$$
$$Asn-Ser(X^4)-R^4-Arg(X^2)-R^{5,4}-Z^1 \qquad 2$$

wherein $X^1$, $X^2$, $X^3$ and $X^4$ and $X^4$ are protective groups, $R^1$, $R^2$ and $R^4$ are as defined in claim 1, $R^{3,4}$ is Ile, Met or Met(O), $R^{5,4}$ is des-$R^{5,4}$ or Tyr($R^5$) wherein $R^5$ is a protective group, $Y^1$ is S-(lower alkylene)-CO or $R^7$-Cys wherein $R^7$ is H-Ser($X^4$)-Ser($X^4$), H-Arg($X^2$)-Ser($X^4$)-Ser($X^4$), H-Arg($X^2$)-Arg($X^2$)-Ser($X^4$)-Ser($X^4$), H-LeuArg($X^2$)-Arg($X^2$)-Ser($X^4$)-Ser($X^4$) or H-Ser($X^4$)-Leu-Arg($X^2$)-Arg($X^2$)-Ser($X^4$)-Ser($X^4$) wherein $X^2$ and $X^4$ are protective groups, and $Z^1$ is hydroxy, amino, lower alkylamino or a linking group which is linked to a solid resin support; followed by deprotecting and oxidizing the intermediate of formula 2 by known processes to give the corresponding peptide of formula 1; and, if desired, transforming the peptide of formula 1 into a therapeutically acceptable salt.

10. A process for preparing the linear protected intermediate of formula 2 of claim 9 in which Z is hydroxy or amino, which comprises:

stepwise coupling in the order of the sequence of the intermediate, the protected amino acid residues or peptide fragments, and, if required, the appropriate protected ω-mercaptoalkanoyl residue, in which:

(1) labile side chain groups of the residues or fragments are protected with suitable protective groups to prevent chemical reactions from occuring at that site until the protective group is ultimately removed after the completion of the stepwise coupling, and (ii) an α-amino group of a coupling reactant is protected by an α-amino protective group while the free carbonyl group of that reactant couples with the free α-amino group of the second reactant; the α-amino protective group being one which can be selectively removed to allow the subsequent coupling step to take place at that α-amino group;

to obtain the linear protected intermediate of formula 2.

* * * * *